United States Patent
Stabile et al.

[11] Patent Number: 5,854,684
[45] Date of Patent: Dec. 29, 1998

[54] MASSIVELY PARALLEL DETECTION

[75] Inventors: Paul J. Stabile, Langhorn; David Norman Ludington, Newtown; Pamela Kay York, Yardley, all of Pa.; Arye Rosen, Cherry Hill, N.J.; Satyam Choudary Cherukuri, Cranbury, N.J.; Peter John Zanzucchi, Lawrenceville, N.J.; Paul Heaney, Plainsboro, N.J.

[73] Assignee: Sarnoff Corporation, Princeton, N.J.

[21] Appl. No.: 721,432

[22] Filed: Sep. 26, 1996

[51] Int. Cl.⁶ .................................................. G01N 21/00
[52] U.S. Cl. ............................ 356/440; 356/417; 356/73
[58] Field of Search ......................... 422/82.05; 436/518; 356/246, 343, 369, 440, 73, 417; 369/112, 44.12, 44.14, 44.23, 44.24, 44.37; 250/559.01, 559.09, 206.1, 208.1; 349/70, 57

[56] References Cited

U.S. PATENT DOCUMENTS

| | | | |
|---|---|---|---|
| 5,233,174 | 8/1993 | Zmek | 250/201.9 |
| 5,428,451 | 6/1995 | Lea | 356/417 |
| 5,461,481 | 10/1995 | Bowen et al. | 356/430 |

FOREIGN PATENT DOCUMENTS

WO 96/05488  2/1996  WIPO.

*Primary Examiner*—Jeffrey Stucker
*Attorney, Agent, or Firm*—William J. Burke

[57] ABSTRACT

The invention provides apparatuses for detecting light from, for example, closely spaced detection sites. In one embodiment, the invention provides an apparatus for measuring the amount of light emitted from a first set of two or more detection sites on a planar substrate while spatially resolving the measurements from each first set detection site, the apparatus comprising: a source of a light beam directed towards the planar substrate at a first angle; one or more lenses for focusing light emitted or reflected from each of the first set detection sites and having a second angle having an angle offset from the first angle, onto a unique area of an array detector; and the array detector comprising a plurality of light responsive pixels, wherein for each first detection site there is at least one light responsive pixel that receives light emitted or reflected from that detection site and substantially no cross-talk from another detection site, and wherein substantially none of the light from the light source intersects with the array detector.

20 Claims, 12 Drawing Sheets

MASSIVELY PARALLEL DETECTION

The present invention relates to a detection device to detect in parallel light emitted from or transmitted from a plate containing a plurality of detection sites, preferably detection wells containing a liquid sample.

In Zanzucchi et al., "Liquid Distribution System," U.S. patent application Ser. No. 08/556,036, filed Nov. 9, 1995 (the '036 Application), a microfluidics system is described that can direct, in a micro-scaled device, reactants to thousands of reaction sites. In Demers et al., "Plate for Reaction System," U.S. application Ser. No. 08/630,018, filed Apr. 9, 1996 (Docket No. DSRC 12098), high-density reaction plates for use with the liquid distribution system of the '036 application are described. In one preferred embodiment, the plates have 10,000 reaction wells on a 4×4 inch surface. Thus, recent developments by Zanzucchi et al. and Demers et al. have produced apparatuses for conducting thousands of reactions in parallel. But this advance is of limited use if there is no way to comparably detect in parallel associated analytical reactions or processes. Some of the issues that interfere with convenient detection in high density plates are (a) the difficulty in identifying individual detection sites, (b) the difficulty in eliminating cross-talk of optical information from closely-spaced detection sites, and (c) the separate collection into addressable locations of optical data from a large number of detection sites.

The present invention solves the detection problem by providing a detector array that can collect in parallel, in a spatially addressable manner, light from a plurality of sites. Thus, for instance, light from 2,500 separate sites can concurrently be collected on an array containing 2,500 separate light responsive pixels that convert the light to an electrical charge, each such pixel being uniquely aligned for receiving light from one of the sites. The separate charges can be separately addressed, measured and converted to a digitally storable, electronic form.

SUMMARY OF THE INVENTION

As a first embodiment, the invention provides an apparatus for measuring the amount of light emitted or reflected from a first set of two or more detection sites on a planar substrate while spatially resolving the measurements from each first set detection site, the apparatus comprising: a source of a light beam directed towards the planar substrate at a first angle; one or more lenses for focusing light emitted or reflected from each of the first set detection sites and having a second angle having an angle offset from the first angle, onto a unique area of an array detector; and the array detector comprising a plurality of light responsive pixels, wherein for each first detection site there is at least one light responsive pixel that receives light emitted or reflected from that detection site and substantially no cross-talk from another detection site, wherein substantially none of the light from the light source intersects with the array detector. In one preferred embodiment, where the source of the light beam and the array detector are located on the same side of the planar substrate, the offset second angle is also offset from the angle at which light of the first angle reflects off the planar substrate. Preferably, the apparatus is designed for use where the emitted or reflected light has a different wavelength than light from the source of light and the apparatus further comprises a filter interposed between the detection sites and the array detector, which filter selectively absorbs the light from the light beam source and transmits light emitted or reflected from the detection sites. Preferably, the source light is collimated to increase the accuracy with which the optics minimize cross-talk between detection sites. In one preferred embodiment, the source of light comprises a beam expander, such as a lens, for expanding the cross-sectional area of the light. Preferably, where the source of light comprises multiple light producing devices, each light source has a collimating lens. Each light producing device can have an optical wavelength doubler or an optical wavelength tripler.

Preferably, the apparatus further comprises an electrical storage device comprising the plurality of storage registers coupled to the array detector for storing the data from the array detector. Preferably, the apparatus is designed for use with the planar substrate wherein the material between each detection site of the substrate is a blocking material that is opaque or non-reflective to the light from the light source such that substantially no light having the second angle emanates therefrom.

Preferably, the detector array has sufficient light responsive pixels and is designed to work with a planar substrate having sufficient separation between the detection sites so that: (a) there are first light responsive pixels of the detector array that are aligned to receive light emitted or reflected from the first set detection sites; and (b) there are second light responsive pixels of the detector array that receive substantially no light because they are aligned with an area of blocking material, such that for each first set detection site there is a grouping of one or more first light responsive pixels receiving light therefrom and this grouping is separated from the grouping for any other first set detection site by at least one second light responsive pixel. In other words, the spacing between the detection sites is sufficient so that the area mapped onto the detector array for the blocked areas between detection sites is at least about one pixel wide.

Preferably, the detector array has sufficient light responsive pixels aligned with each first set detection site so that the light emitted or reflected from the detection site can be spatially resolved to detect differences across the detection sites in the quantity of light emitted or reflected therefrom. Preferably, at least about twenty-five light responsive pixels are aligned to receive light from each first set detection site.

Preferably, the array detector comprises a photon-based imaging device, which is preferably a charge coupled device (CCD), an intensified CCD array, a focal plane array, a photodiode array or photodetector array.

In one embodiment, the light source is located on one side of the planar substrate and the array detector is located on the other. In another embodiment, the light source and the array detector are located on the same side.

Preferably, the detection sites comprise chambers suitable for holding a liquid. Preferably, the apparatus is designed for use with planar substrates having detection sites that are concave depressions for holding liquid, wherein the surfaces on the depressions have a coating of one or more layers of material, wherein the coating is designed to reflect the light emitted or reflected from the detection sites. In one embodiment, the shape of the concave detection sites functions to direct a substantial part of the reflected light towards the aligned pixels. In one version of this embodiment, the light source is designed to position beneath the planar substrate and the coating is designed to transmit the source light.

Preferably, the light source comprises one or more lasers, diode lasers, light emission diodes or superluminescent diodes.

The apparatus is preferably designed to detect light emitted or reflected from, or transmitted through, at least about 100 detection sites of the first set and has at least one light responsive pixel aligned with each detection site of the first set. Preferably, the source of light directs at least about 0.1 mW of light to each detection site of the first set, more preferably at least about 1 mW to each detection site. Preferably, the apparatus is designed to detect light from all of the detection sites of the first set within about ten seconds, more preferably within about one second. Preferably, the apparatus is designed to detect light emitted or reflected from, or transmitted through, at least about 1,000 detection sites of the first set, more preferably at least about 4,000 detection sites, still more preferably at least about 10,000 detection sites, yet more preferably at least about 100,000 detection sites, still yet more preferably at least about 1,000,000 detection sites, and has at least one light responsive pixel aligned with each detection site of the first set.

In one embodiment, the source of light comprises at least one light producing device per detection site. In another embodiment, the one or more focusing lenses comprise a separate lenslet overlaid on the light responsive pixels aligned with each first set detection site.

In one embodiment, the apparatus is suitable for use in colorimetric, fluorescence, chemiluminescence, fluorescence polarization, time-resolved fluorescence, fluorescence correlation spectroscopy or confocal fluorescence. In confocal fluorescence the optics are finely tuned to carefully control the depth of field such that fluorescence is only detected from a narrow slice within a detection site. Fluorescence correlation spectroscopy is a subset of confocal fluorescence where fluorescence is only detected from a narrow cross-section of the slice.

In one preferred embodiment, the apparatus further comprises electronic storage device comprising the plurality of storage registers coupled to the array detector for storing the data from the array detector; a processor having access to the stored data; and a motor for moving the substrate, light source or array detector under the control of the processor, wherein the processor is programmed to use one or more initial illuminations of the substrate with the source light to generate data which the processor uses to operate the motor to correct the alignment of the light source, first set detection sites and array detector. Preferably, the processor is programmed to illuminate a first calibration plate having uniform content at its detection sites, which content emits light in response to the illumination, and to collect the data generated by the illumination to diagnose irregularities in the amount of light directed to each detection site and to establish normalization parameters for correcting experimental values for the irregularities in illumination. Preferably, the processor is programmed to illuminate a second calibration plate having uniform content at its detection sites, which content emits substantially no light in response to the illumination, and to collect the data generated by the illumination to calculate the amount of detected light emission that is not due to the experimental content at the detection sites. If the experimental protocols used with the planar substrates produce detection site contents that are individually sufficiently homogeneous, then calibration procedures and software can be used to normalize for the effects of cross-talk.

Preferably, the offset between the first and second angles is from at least about 10° to about 180°.

The invention also provides assay systems made up of the above-described apparatus and reaction plates having a substantial number of densely arrayed reaction cells, as described below, for which the apparatus is designed to make optical measurements. For example, the invention provides such and apparatus and a plate having a first edge and a second edge and having at least about 1,000 uniformly sized reaction cells formed in its upper surface, wherein the density of the reaction cells is at least about 10 cells per $cm^2$, wherein the apparatus is designed to detect light emitted or reflected from the uniformly sized reaction cells.

As a second embodiment, the invention further provides an apparatus for measuring the amount of light emitted from a first set of two or more detection sites on a planar substrate while spatially resolving the measurements from each first set detection site, the apparatus comprising: a source of a light beam having a first wavelength directed towards the planar substrate at a first angle; one or more lenses for focusing light emitted from each of the first set detection sites and having a second angle onto a unique area of an array detector; a filter interposed between the detection sites and the array detector, which filter selectively absorbs light of the first wavelength and transmits light emitted from the detection sites having a wavelength differing from the first wavelength; and the array detector comprising a plurality of light responsive pixels, wherein for each first detection site there is at least one light responsive pixel that receives light emitted from that detection site and substantially no cross-talk from another detection site, wherein substantially none of the light from the light source intersects with the array detector. Preferably, the second embodiment apparatus further comprises: a first polarizing filter for polarizing the source light beam to a first polarity; and a second polarizing filter for polarizing the light emitted from the detection sites to a second polarity, which is offset from the first polarity, preferably by about 90°.

As a third embodiment, the invention further provides a method for measuring and spatially resolving the amount of light transmitted through a first set of two or more detection chambers or the amount of light emitted from the first set detection sites as a result of their illumination, wherein each chamber is separated by a blocking material that is opaque to the light and the density of first set detection sites is at least about 10 per $cm^2$ preferably at least about 20 per $cm^2$, more preferably at least about 40 per $cm^2$, still more preferably at least about 100 per $cm^2$, the method comprising (1) providing an apparatus comprising: a source of light directed towards the planar substrate at a transmission angle; one or more lenses for focusing light from each first set detection chamber onto a unique area of an array detector; and the array detector comprising a plurality of light responsive pixels, wherein for each first set detection chamber there is at least one light responsive pixel that receives light transmitted through that detection chamber and substantially no cross-talk from another detection chamber, and (2) measuring light transmitted through the detection sites using the apparatus.

In one embodiment of the method of the third embodiment, the source of light is operated to direct a pulse of light towards the first set detection sites and thereafter a light response is collected in the array detector while the source of light is not producing light. In a preferred embodiment, the apparatus is designed for use with planar substrates having detection sites are concave depressions for holding liquid, wherein the surfaces on the depressions have a coating of one or more layers of material, wherein the coating is designed either to reflect the light emitted from the detection sites or light from the source of light.

In a fourth embodiment, the invention further provides an apparatus for measuring and spatially resolving the amount of light emitted from a first set of two or more detection sites arranged on a planar substrate with a density of at least about 10 detection sites per $cm^2$, the apparatus comprising: one or more lenses for focusing light emitted from the first set detection sites, which light has a detection angle, onto an array detector; and the array detector comprising a plurality of light responsive pixels, wherein for each detection site there is at least one light responsive pixel that receives light emitted from that detection site and substantially no crosstalk from another detection site. Preferably, the density of detection sites is at least about 20 per $cm^2$, more preferably at least about 40 per $cm^2$, yet more preferably at least about 100 per $cm^2$. In one embodiment, wherein either the planar substrate incorporates a scintillate adjacent to each detection site or the detection sites comprise chambers suitable for holding a fluid containing a scintillate. It will be recognized that all preferred or alternative features of other embodiments or aspects (described below) that are appropriately applied to another embodiment or aspect are also preferred or alternative embodiments for that other embodiment or aspect.

DEFINITIONS

Figure 1A:
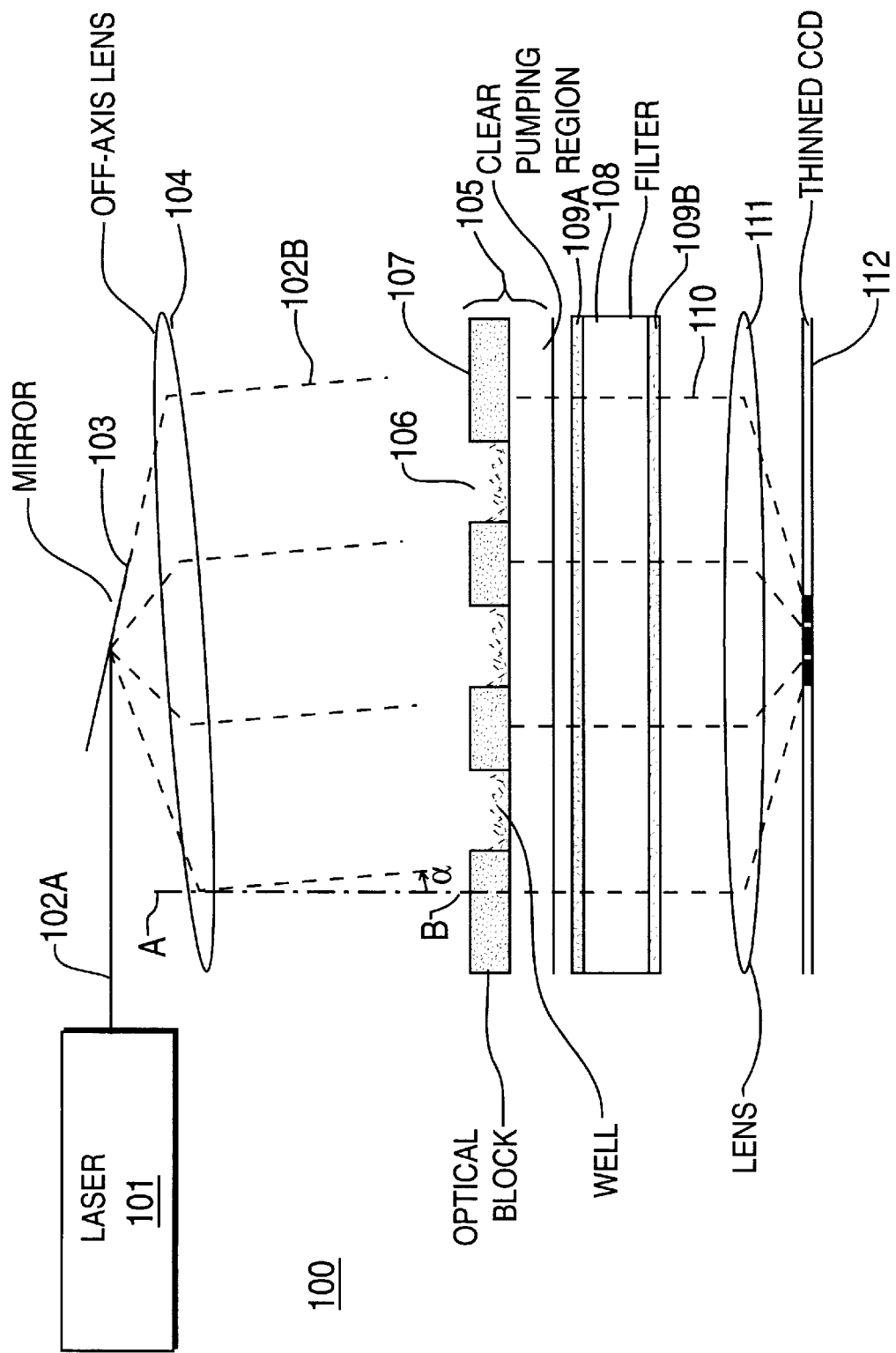
FIGS. 1A and 1B depict detection devices of the invention.

The following terms shall have the meaning set forth below:

addressable source of a beam of light

Addressable sources of light beams are: produced by a number of light-emitting devices that can be sequentially powered in sub-groups (which can include only one such device) until all of the light-emitting devices have been powered; or are light beams that are divided out of one or more broader light beams by mechanically moving a mask between the planar substrate and the one or more broader beams of light; or are beams that are divided out of one or more broader beams by interposing, between the one or more broader beams of collimated light and the planar substrate, a device having a plurality of windows with electrically operated shutters. Preferably either each light source can separately illuminated or all the light sources of about whole number subsets (such as subsets of about ½, ⅓, ¼, ⅕, ⅙, ⅐, ⅛, etc. of the light sources) can be illuminated in concert.

adjacent detection sites

A detection site is adjacent to any reference detection site if a straight line joining the center of the detection site to the reference detection site is no more than about 1.5 times the length of the line joining the center of the reference detection site to the center of the nearest detection site.

alignment of detection sites or detection areas with light responsive pixels

A detection site or detection area is aligned if all the light of the second angle, transmission angle or detection angle (excepting nominal transmission loses) emitted or transmitted therefrom intercepts the aligned light responsive pixels.

angle of light

The "angle of light" is measured by comparing the angle of a reference vector with a vector describing the motion of the light.

beam expander

One or more lenses or other optical devices through which a beam of collimated (parallel) light of a first cross-sectional area is expanded to a beam of collimated light having a greater, second cross-sectional area.

detection site

An area or volume on a substrate on or in which a chemistry or biochemistry has been conducted that either (a) will produce a substance that is directly or indirectly (for instance, a radioisotope detected with a scintillate or fluorophore) detected optically or (b) will or will not produce such a substance depending on such circumstances as whether a material used in the chemistry or biochemistry contains a substance which the user of the apparatus of the invention seeks to analyze, whether the materials used in the chemistry or biochemistry inhibit production of the substance, whether the chemistry or biochemistry functioned as anticipated, and the like.

directly focuses a beam of light

An addressable source of a light beam directly focuses a light beam if, after any optical devices needed to collimate the light, no other optical devices other than light filters intervene between the device producing the light and the substrate.

experimental measurement

A measurement of the light transmitted through or emitted from a detection site to determine a data point, for instance for a chemical or biochemical procedure conducted on the planar substrate, as opposed to an initial, calibration or alignment measurement used to establish that a light detection apparatus is properly aligned and in good working order.

light responsive pixel

A defined area of material that, when exposed to light energy, generates a corresponding collection of charge.

linearly aligned detection sites

"Linearly aligned detection sites" each have an equivalent volume or surface area having geometrical centers aligned along a straight line.

mapping onto the array detector

At any given point in the plane of the planar substrate, light emitted therefrom that focuses on a particular pixel is "mapped" onto that pixel.

photon-based imaging device

Any device that converts impinging photons to a charge or voltage, preferably wherein data from the device can be used to determine the number of photons impinging the device.

scintillate

A material that when struck with an appropriate particle or photon such as a nuclear decay particle, for instance an appropriate alpha, beta or gamma particle, emits a light particle.

storage device

Device that electronically stores data, for instance in digital form or in analog form as, for example, on a magnetic tape.

substantially no light emanates from the material between detection sites

Substantially no light emanates from the material between detection sites if such stray light as does emanate from such material does not create a signal in a pixel that is distinguishable from background noise.

substantially no light from the source light

An array detector receives substantially no light from the light source if the light-source light intercepting light-responsive portions of the pixels of the array detector is no more than about 5%, preferably no more than about 1%, more preferably no more than about 0.1%, yet more preferably no more than about 0.01%, of the pixel-intercepting light that originates from the planar substrate.

substantially no cross-talk

There is substantially no cross-talk at a pixel aligned with a detection site if no more than about 5% of the light emitted from an adjacent detection site intercepts the light-responsive portion of the pixel. Preferably, no more than about 1%, more preferably about 0.1%, yet more preferably about 0.01%, of the light emitted from an adjacent detection site intercepts the light-responsive portion of the pixel.

DETAILED DESCRIPTION

First Additional Aspect

In a first additional aspect, the invention provides an apparatus for measuring the amount of light emitted from or transmitted through two or more detection sites of a first set of detection sites on a planar substrate while spatially resolving the measurements for each detection site of the first set, the apparatus comprising: (a) for each detection site of the first set, an addressable source of a light beam directed to that detection site at a first angle; and (b) an array detector comprising a plurality of light responsive pixels, wherein for each detection site of the first set there is at least one light responsive pixel that receives light emitted from or transmitted through that detection site at a second angle that can be the same as the first angle. Preferably, the apparatus further comprises a controller for controlling the addressable beams of light. The controller, preferably, is programmed to operate the light beams so that the light beams for any two adjacent detection sites on the substrate are not simultaneously illuminated during an experimental measurement. Preferably, the controller is programmed to operate the beams of light so each detection site of the first set is illuminated in the course of measuring the light emitted from or transmitted through all of the detection sites of the first set.

In a preferred embodiment, the controller further collects data from the detector array for a time interval beginning at or after a first group of addressable beams is illuminated until a time before the next group of addressable beams is illuminated and identifies which data from the detector array corresponds to illuminated detection sites. Preferably, the controller (1) illuminates and detects light from the first set detection sites, wherein none of the first set detection sites are adjacent, and (2) then illuminates and detect light from a second, separate set of at least two detection sites, wherein none of the second set detection sites are adjacent. More preferably, the controller (1) illuminates and detects light from the first set detection sites, wherein none of the first set detection sites are adjacent, (2) then illuminates and detect light from a second, separate set of at least two detection sites, wherein none of the second set detection sites are adjacent, (3) then illuminates and detects light from a third, separate set of at least two detection sites, wherein none of the third set detection sites are adjacent, and (4) then illuminates and detects light from a fourth, separate set of at least two detection sites, wherein none of the fourth set detection sites are adjacent.

In one version, the apparatus further comprises one or more lenses for focusing light emitted from or transmitted through the detection sites, which light has the second angle, which can be offset from the first angle, onto the array detector.

In an embodiment of the apparatus, the apparatus is suitable for detecting light emissions from the detection sites that have a wavelength different from that of the beams of light and wherein the apparatus further comprises: (c) a filter that transmits light emitted from the detection sites but absorbs light from the addressable beams of light, wherein the filter is interposed between the substrate and the array detector.

In an embodiment, the apparatus is designed for use with planar substrates having detection sites that are concave depressions for holding liquid, wherein the surfaces on the depressions have a coating of one or more layers of material, wherein the coating is designed to reflect the light emitted from the detection sites. Preferably, the shape of the concave detection sites functions to direct a substantial part of the reflected light towards the aligned pixels. Preferably, the reflective surface is effective for changing the angle of the light transmitted through the chamber from the first angle to the second angle, which second angle differs from the first angle. In an embodiment, the light beam source is designed to position beneath the planar substrate and the coating is designed to transmit the source beam light.

In one embodiment, the apparatus further comprises a motor for controllably moving the substrate, the source of light or the array detector to align the first set of detection sites, and then to align a separate, beta set of detection sites on the planar substrate.

Preferably, there are sufficient sets of detection sites so that no two concurrently illuminated detection sites are close enough to each other to allow significant cross-talk, more preferably cross-talk is about 1% or less, yet more preferably about 0.1% or less, still more preferably about 0.01% or less. Thus, in some embodiments there will be, for example, four sets of detection sites, in others eight sets, and in other 16 or more sets of detection sites, and the apparatus will be operated to separately illuminate the different sets of detection sites. In some embodiments, the separate illumination will require the physical movement a mask, the light source, the planar substrate or the array detector. In other embodiments, electronics will control the separate illuminations by activating separate light sources or opening appropriate shutters, such as liquid crystal windows.

In an embodiment of the invention, the addressable light beam sources comprise a light-emitting device and a mask interposed between the planar substrate and the light source and a motor for moving the mask relative to the substrate, wherein at each of a plurality of stop positions the mask allows one or more beams of light directed to a subset of the detection sites of the first set to pass through to the planar substrate, and wherein all of the detection sites of the first set have been illuminated by a beam of collimated light after the mask has been moved through all of its stop positions.

In another embodiment of the invention, the addressable beam sources comprise: a source of light; and a liquid crystal window array interposed between the planar substrate and the light source and comprising a plurality of liquid crystal windows each having a relatively opaque and a relatively translucent state, wherein the liquid crystal windows can be switched between the two states such that each detection site of the first set can be illuminated through a translucent liquid crystal window without illuminating the immediately adjacent detection sites on the substrate.

In an embodiment of the invention, the beams of collimated light are each provided by a separate light-emitting device that directly focuses a beam of light on a detection site of the first set.

Second Additional Aspect

In a second additional aspect, the invention provides an apparatus for measuring the amount of light emitted from a first set of two or more detection sites on a planar substrate while spatially resolving the measurements from each first set detection site and for measuring the amount of light emitted from a second set of two or more detection sites on a planar substrate while spatially resolving the measurements from each second set detection site, the apparatus comprising: (a) a source of a light beam directed towards the planar substrate at a first angle; (b) a means to separately illuminate the first and second set detection sites; (c) one or more lenses for focusing light emitted from each of the first or second set detection sites and having a second angle having an angle offset from the first angle, onto a unique area of an array detector; and (d) the array detector comprising a plurality of light responsive pixels, wherein for each first set detection site there is at least one light responsive pixel that receives light emitted from that detection site and substantially no cross-talk from another first set detection site, wherein for each second set detection site there is at least one light responsive pixel that receives light emitted from that detection site and substantially no cross-talk from another second set detection site, wherein the first set detection sites are distinct from the second set detection sites.

In one preferred embodiment, the apparatus is designed to first illuminate and detect light from the first set detection sites, and then illuminate and detect light from the second, separate set of at least two detection sites. Preferably, the apparatus further comprises a motor for controllably moving the substrate, the source of light or the array detector and wherein the motor moves the substrate, light source or array detector to first align the detection sites of the first set with the source light and then to align the detection sites of the second set with the source light, so that the light emitted as a result of excitation by the source light from each detection site of the first or second set can be measured.

In some embodiments, the separate illumination of separate sets of detection sites will require the physical movement a mask, the light source, the planar substrate or the array detector. In other embodiments, electronics will control the separate illuminations by activating separate light sources or opening appropriate shutters.

Description of Invention with Reference to the Drawings

In the detection device 100 of FIG. 1A, the source of collimated light is depicted, for example, as a laser 101, that emits light beam 102A. Light beam 102A is bent by mirror 103 and off-axis lens 104 to create a broader beam 102B having an angle a relative to a line A-B that is perpendicular to the planar substrate 105. Portions of light beam 102B intercept the detection sites 106 where the light from the beam 102B can be absorbed by molecules at the detection sites, and portions of light beam 102B intercept areas 107 that are covered with optical blocking material. Light 110 emitted from the detection sites 106 at an angle β relative to line A-B (in the illustration, β is 0 degrees) passes through filter 108. Filter 108 is coated on first side 109A and second side 109B with an optical coating. Filter 108 is selected to absorb light of the wavelength of beam 102B, and to transmit light of the wavelength of beam 110. Light beam 110 is focused by lens 111 onto array detector 112, which is illustrated as a charge-coupled device (CCD). The lens 111 fails to focus light of angle a onto the array detector 112.

Figure 1B:
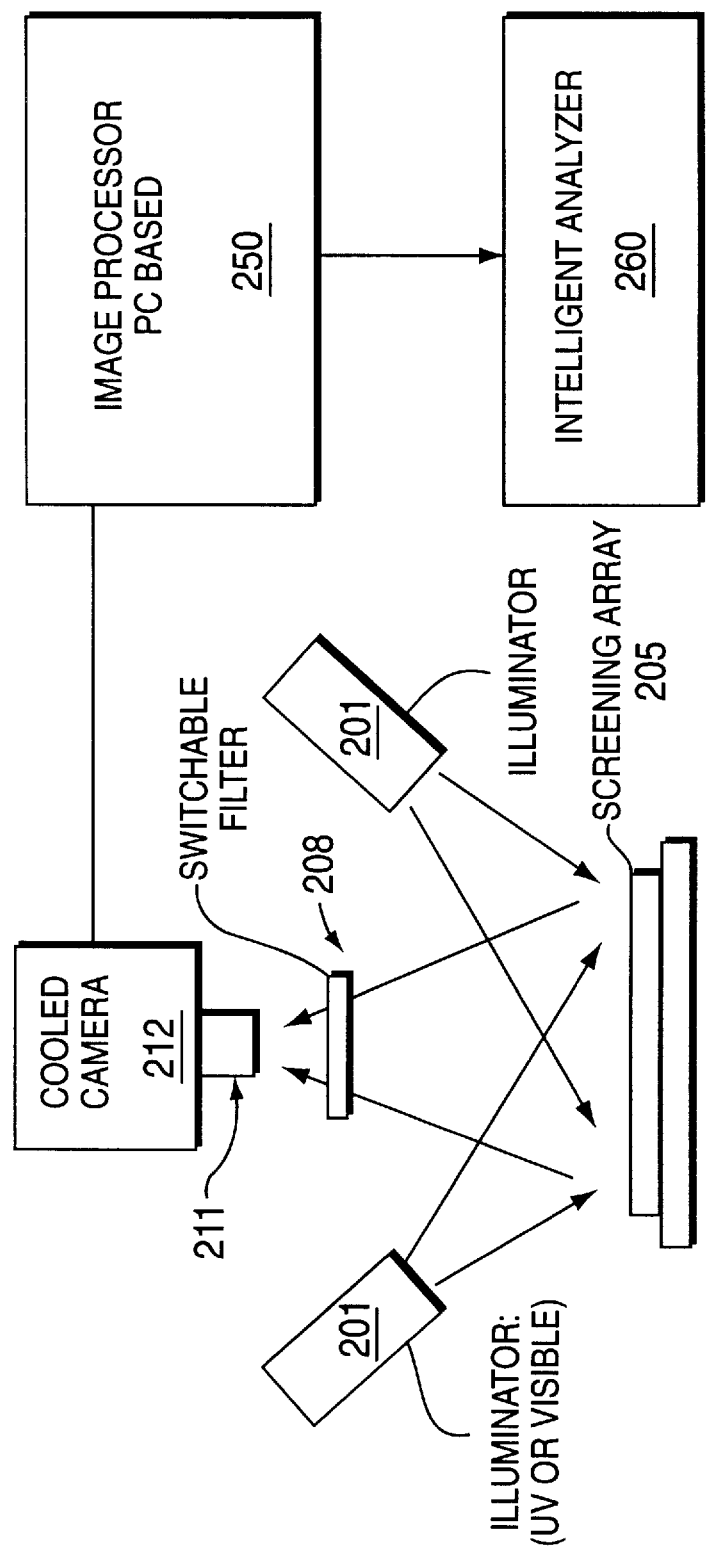

FIG. 1B shows an alternative embodiment wherein the light beam source 201 is located on the same side of planar substrate 205 as the array detector 212. Interposed in front of the array detector is a filter 208 and a lens 211. The data from the array detector 212 is processed by image processor 250 and analyzed by analyzer 260.

Figure 2:
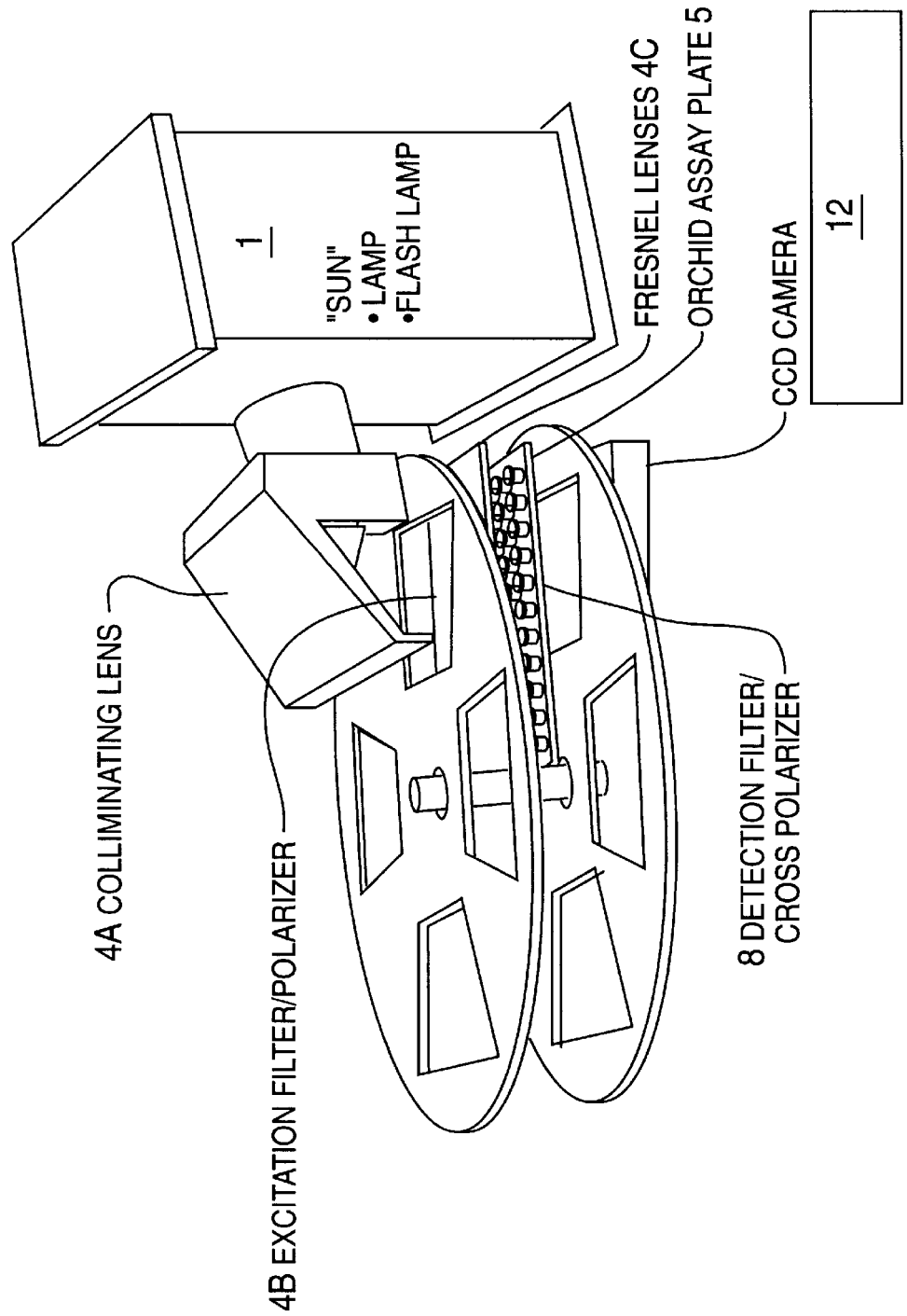
FIG. 2 shows another detection device of the invention.

In FIG. 2 is shown an alternative embodiment of the device wherein the polarity of the excitation light is used to distinguish it from emissions. Light source 1 can for instance be a Xenon Short Arc Lamp available from Oriel Instruments Corp. (Stratford, Conn., e.g., the 300W lamp Model Number 6259) and suitable for emitting large amounts of excitation energy. Colliminating lens 4A also serves to redirect light from the light source 1 towards assay plate 5. An light filter and polarizer 4B is located between the colliminating lens 4A and the assay plate 5, and serves to select light of an excitation wavelength and of a first polarity. A set of fresnel lenses 4C is located between the light filter and polarizer 4B and the assay plate 5. The fresnel lenses serve to focus the excitation energy onto each individual well in the assay plate. Another set of lenses can be used to collect the emission light from the assay plate and focus it on the CCD camera. A filter and crosspolarizer 8 is located between the assay plate 5 and a CCD 12, and serves to select light of an emission wavelength and a second polarity offset from the first polarity.

Figure 3A:
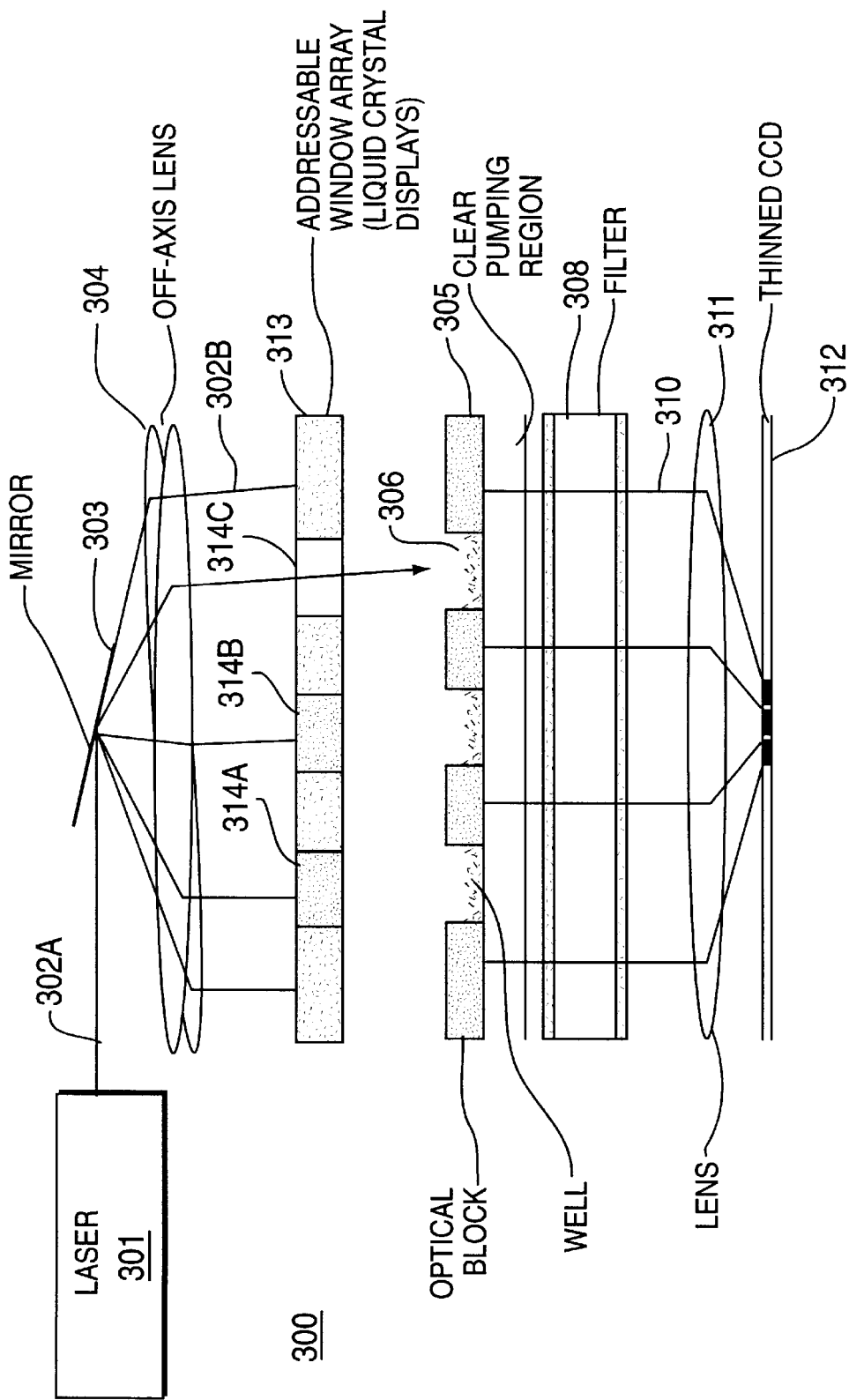
FIGS. 3A and 3B depict another detection device of the invention.

In the detection device 300 of FIG. 3A, the features depicted in FIG. 1A are maintained and are indicated by corresponding numbers obtained by adding 200 to the feature numbers of FIG. 1A. However, the detection device 300 differs in having an addressable window array 313 interposed between (a) the light source 301, mirror 303 and lens 304 and (b) the planar substrate 305. The addressable window array 313 has closable transmission windows 314. Illustrated are first transmission window 314A, second transmission window 314B and third transmission window 314C. First transmission window 314A and second transmission window 314B are illustrated as closed, while third transmission window 314C is illustrated as open.

Figure 3B:
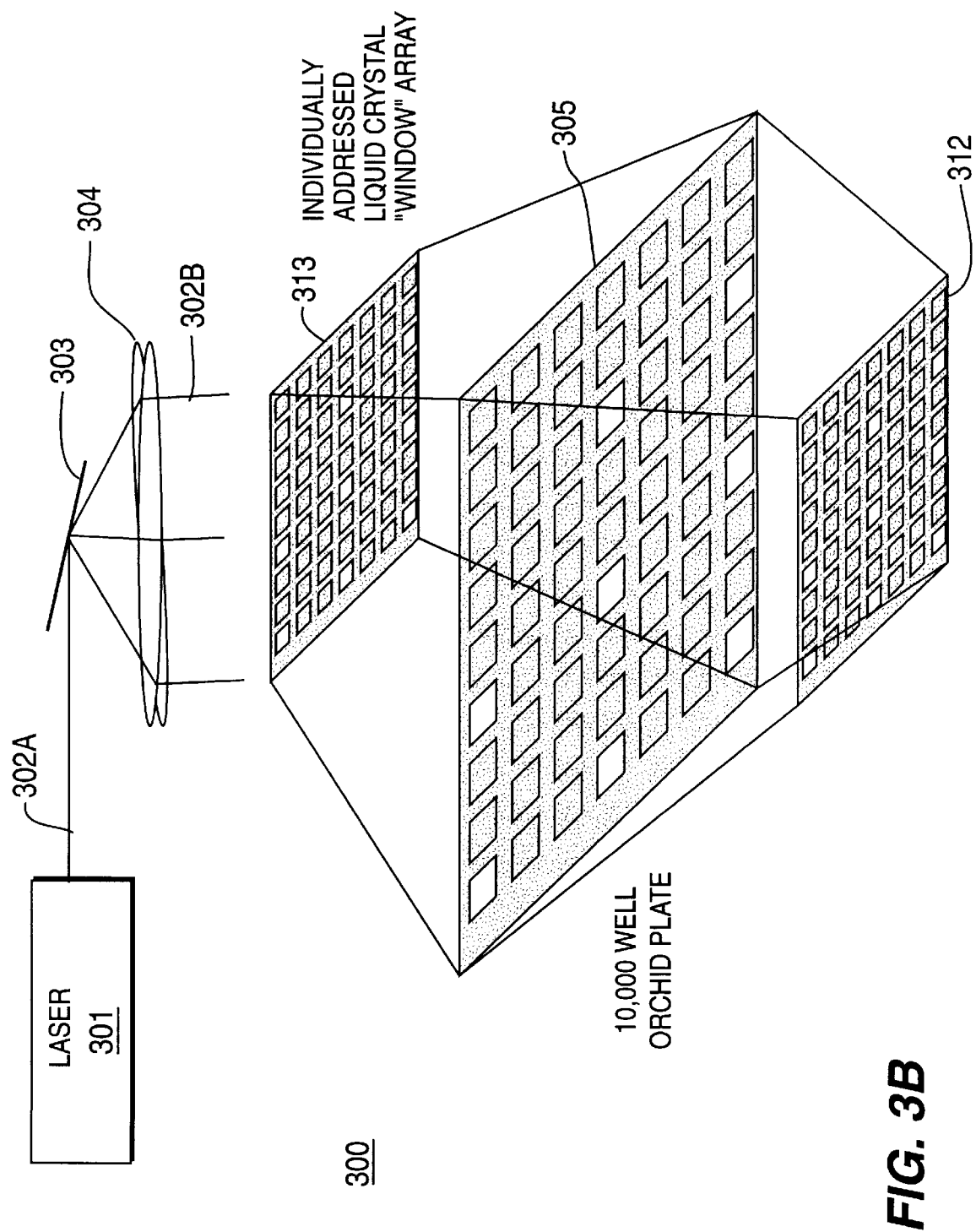

FIG. 3B shows three-dimensional aspects of detection device 300, and illustrates that a patterned array transmission windows 314 can be opened at a given moment. As illustrated, only a subset of detection sites are illuminated at any given moment. Thus, for instance, all concurrently illuminated detection sites can be separated by one unilluminated detection site such that a total of four illuminations are needed to illuminate all the detection sites. If the illuminated detection sites are separated by two un-illuminated detections sites, then nine separate illuminations are needed to illuminate all of the detection sites; if the illuminated detection sites are separated by three un-illuminated detections sites, then 16 separate illuminations are needed to illuminate all of the detection sites; and so on. The effect of cross-talk can be minimized by re-initializing the array detector if needed between illuminations.

Figure 4:
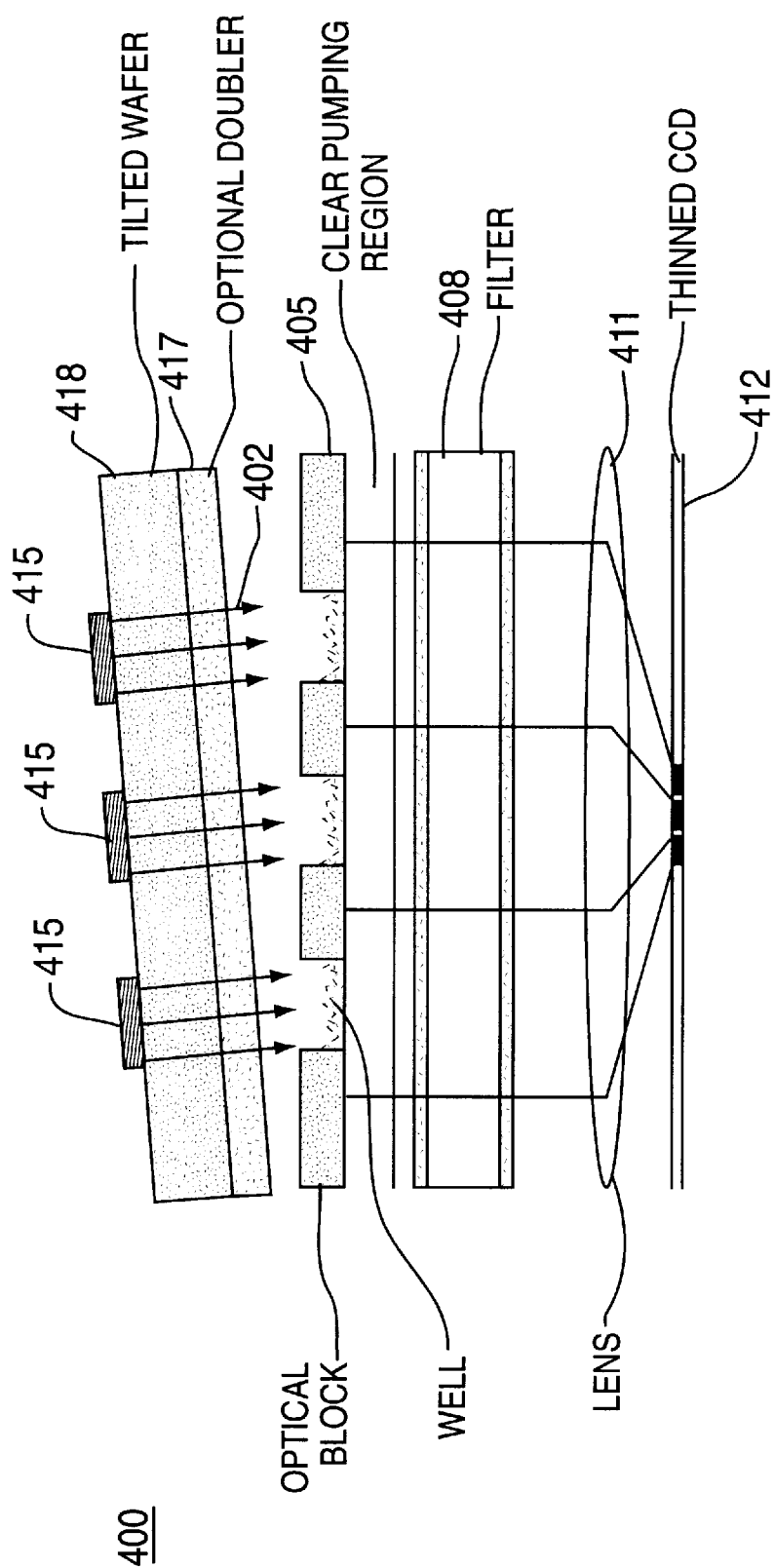
FIG. 4 shows another detection device of the invention.

FIG. 4 shows a detection device 400 which provides an individual, addressable light source 415 for each of all or a subset of the detection sites 406. The light sources 415 are set in a light source support substrate 418. Each light source 415, which for instance are light-emitting diodes (LEDs), emits collimated light 402 of angle α. The light can be collimated using individual collimating lenses 416 (not shown) overlaid onto each light source 415. As illustrated, each lens can be overlaid with an optical doubler 417. The individually activatable light sources 415 can be used to minimize cross-talk in the same way that individual illumination reduces cross-talk in detection device 300.

Figure 5:
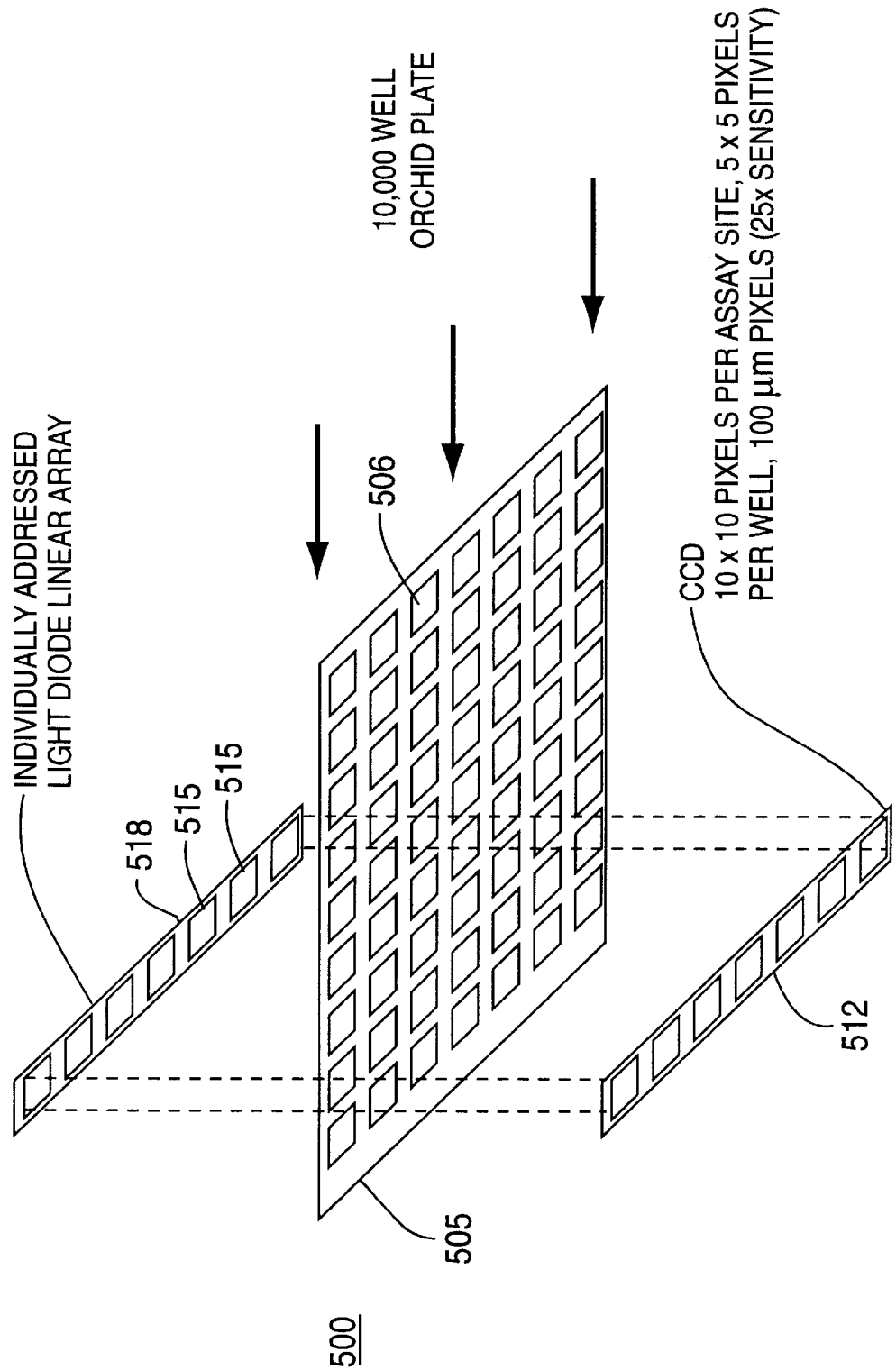
FIG. 5 depicts another detection device of the invention.

FIG. 5 shows a detection device 500 which provides an individual, addressable light source 515 for each of a subset of the detection sites 506. For illustration, the light source support substrate 518 has light sources 515 for each detection site 506 located in a row on the planar substrate 505. Detection device 500 can operate without making use of offset angles for the source and emitted light illustrated in detection devices 100, 300 and 400. Instead, detection device 500 relies on individual illumination of the detection sites to minimize crosstalk. To collect data for each detection site, the plate is moved relative to the light sources 515 and the detector array 512, and the associated electronics are operated at each alignment of the light sources 515 and detector array 512 with a row of detection sites 506, until data has been collected from all detections sites 506. It will be recognized that a number of light source support substrates 518 and associated array detectors 512 can be present in a detection device. For instance, where the planar substrate 505 has 100 by 100 (=10,000) detection sites 506, ten light source substrates 518 each with 100 light sources can be used to illuminate all 10,000 detection sites after 10 separate physical alignments of the detection sites 506.

Figure 6:
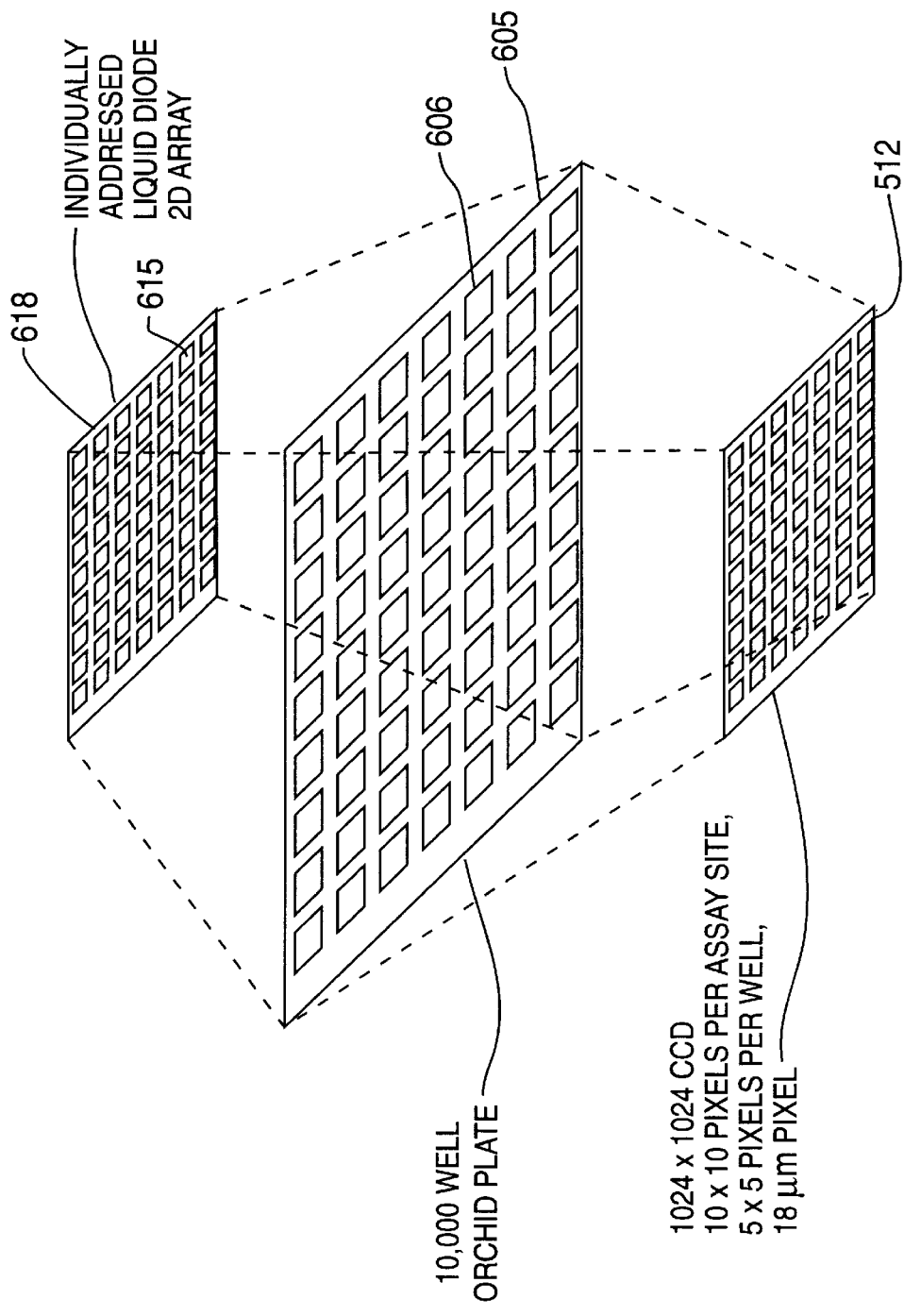
FIG. 6 depicts another detection device of the invention.

FIG. 6 shows a detection device 600 having a 2-dimensional array 618 of individually addressable light sources 615, each aligned with a separate detection site 606, preferably via an intervening optical device 604 which further separates the light beams 602 emitted by the light sources 615. For instance: the planar substrate 605 can contain a 100×100 array of detection sites; the detector array 612 can be a 1024×1024 CCD having 10×10 light-responsive 18 μm pixels per the average area on the planar substrate 605 occupied by a detection site 606 (where the detection sites 606 are laid out in columns and rows, this average area is the area defined by the multiplication product of (1) the pitch between reaction cells in separate rows and (2) the pitch between reaction cells in separate columns); and the detector array 612 can have 5×5 pixels aligned with each detection site.

Figure 7:
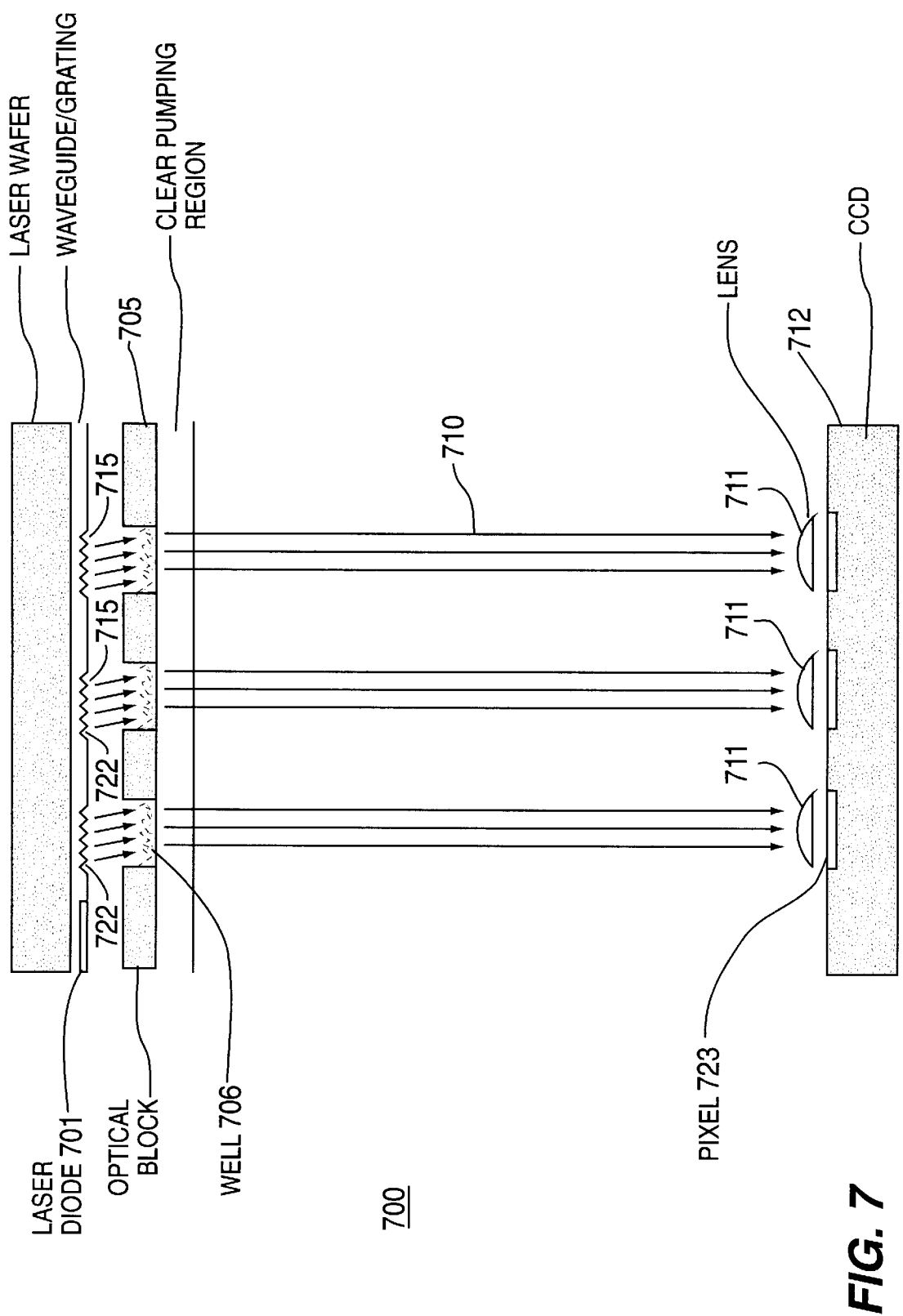
FIG. 7 depicts another detection device of the invention.

FIG. 7 shows a detection device 700 where light sources 715 are provided by separate waveguides 722 (such as gratings) that direct light from a laser diode 701. Each pixel 723 in this embodiment has an overlaid lens 711 for selecting light of the second angle.

Broad beamed light sources such as the Xenon Arc Lamp flood the entire Assay plate with one beam of light. In a light source that is made up of an array individual light beams, each light beam typically corresponds to a detection site in the assay plate. Each beam is addressable (can be turned on or off separately from the other beams). Individually addressable LEDs can be constructed by packaging individual LEDs of suitable dimensions on a circuit board allowing the individual illumination either of each LED or a subset of the LEDs. For example, the semiconductor laser diodes (visible and infrared wavelengths) available from Opto Power Corporation (Tucson, Ariz.) or SDL, Inc. (San Jose, Calif.) can be so packaged. Alternatively, such LEDs with emitter center-to-center dimensions of 14 micrometers or 100 micrometers are available pre-packaged in multiples of 4 from SDL, Inc. For such relatively closely spaced light emitters, optics are generally used to direct the individual beams towards the more widely spaced-apart detection sites. The closely packed emitters have advantages in cost and simplicity of the housing requirements. Where each emitter will be directly aligned with a detection site, preferably the center-to-center dimension used in the present application ranges from about 0.5 mm to about 1.2 mm. In various embodiments, preferred ranges are from about 1.0 mm to about 1.2 mm, from about 0.7 mm to about 0.9 mm, or from about 0.5 mm to about 0.7 mm.

The array detector can be, for example, a charge coupled device (CCD, such as that available from DALSA, Inc. (Easton Conn.), David Sarnoff Research Center (Princeton, N.J.) or Princeton Instruments (Trenton, N.J.)), an intensified CCD array (such as that available from Princeton Instruments, Hamamatsu Corp. (Bridgewater, N.J.) or Photometrics Ltd. of Tucson, Ariz.), a focal plane array (such as that available from Scientific Imaging Technologies, Inc. (Beaverton, Ore.), Eastman Kodak Co., Inc. (Rochester, N.Y.) or David Sarnoff Research Center), a photodiode array (such as that available from Reticon Corp. (Sunnyvale, Calif.), Sensors Unlimited, Inc. (Princeton, N.J.) or Hamamatsu) or photodetector array (such as that available from FLIR Systems Inc. (Portland, Ore.), Loral Corp. (New York, N.Y.), or Hughes Electronic Corp. (Los Angeles, Calif.)).

As will be recognized, cooling can be used to increase sensitivity. Preferably, the light responsive pixels are maintained at a temperature of about 10° C. or less, more preferably a temperature from about −30° C. to about 0° C. The detector preferably has the following performance features:

quantum efficiency of at least about 10%, more preferably at least about 70%;

responsiveness to light from about 350 nm to about 1100 nm;

optical fill factor of at least about 100%;

at least about 300,000 electrons per full well;

no more than about 12 electrons per pixel noise at 1 Mhz clock rates (50 fps);

quantitative dynamic range of at least about 88 dB at 50 fps;

at least about 2000× antiblooming capability;

at least about 1% vertical and 2% horizontal response uniformity.

Masks, such as those incorporated into the planar substrate to optically separate the various detection sites can for instance be manufactured by forming the planar substrate of two layers of material. The top layer is formed of a material that is opaque to the relevant wavelengths, while the second is translucent to light of the wavelength to be detected. The top layer is chemically etched or formed by laser ablation to define open areas that will define wells that serve as light-transmitting apertures. After such structures have been formed, this top masking layer is bonded to the lower, translucent layer. A method for forming such a bond are set forth in "Field-Assisted Sealing," U.S. Application P-89, 876, filed Nov. 7, 1995, which patent application is incorporated by reference, in its entirety, into this specification. Additional sealing methods are described, for example, in Jobling-Purser, U.S. Pat. No. 2,620,598, Curlee et al., U.S. Pat. No. 5,009,690, Kleiman, U.S. Pat. No. 4,643,532, Pomerantz, U.S. Pat. No. 3,506,424, Pomerantz et al., U.S. Pat. No. 3,417,459, Horne, U.S. Pat. No. 4,294,602 and Wohltjen et al., U.S. Pat. No. 4,452,624. LCD masks are described, for example, in Stewart et al., U.S. Pat. No. 5,076,667 and Roach et al., U.S. Pat. No. 5,337,068.

The planar substrate 105, 305, 405, 505 or 605 (for convenience, hereafter 105) used with the invention is formed of a substrate that is an organic or inorganic material that is suitable for forming the fine structures described herein. The planar substrate 105 should be formed of a material that is resistant to the types of materials it is anticipated will be encountered in use. Thus, for instance, in diagnostic settings the planar substrate 105 typically encounters aqueous materials and can, accordingly, be manufactured of a broad range of materials. Where the planar substrate 105 is designed for use in synthetic reactions, often the planar substrate 105 should be constructed of a material that is resistant to acids, bases and solvents. In one preferred embodiment, the planar substrate 105 is constructed of glass, particularly borosilicate glass.

A basic parameter for the planar substrate 105 is the spacing between the centers of adjacent detection sites 106, which spacing is termed the "pitch." Four cell formats for plates are illustrated in FIG. 7; these formats are the 1K, 4K, 10K and 100K formats. The 1 K format has a pitch of 2260 $\mu$m; the 4K format has a pitch of 1488 $\mu$m; the 10K format has a pitch of 965 um; and the 100K format has a pitch of 558 $\mu$m. Illustrative parameters for these formats are set forth below:

found on a planar substrate 105 that is separable from the portion of the liquid distribution system containing reservoirs and pumps. The separable planar substrate 105 docks with the liquid distribution system, typically with a gasket material (that has openings at appropriate locations) interposed between the two, so that the cells are aligned underneath the appropriate outlet for delivering liquid from the liquid distribution system.

Three parameters that are basic to the format of the planar substrate 106 are the spacing between detection sites 106 (i.e., pitch), the area of each of the openings of the detection sites 106 which will be referred to as the cell aperture, and the row-column arrangement which will be referred to as the matrix layout. The depth of a detection site 106 can be made to vary according to the application for which the planar substrate 106 is used. Structures required for support functions can be formed on the area between detection site apertures.

Figure 8:
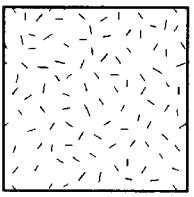
FIG. 8 shows some illustrative formats for the planar substrate used with the invention.

Designs of particular interest can be met by the matrix formats of 1,000 detection sites 106 represented by a matrix of 32×32=1,024 detection sites 106; 4,000 detection sites 106 represented by a matrix of 64×64=4,096 detection sites 106; and 10,000 detection sites 106 represented by a matrix of 100×100=10,000 detection sites 106. Such designs are illustrated in FIG. 8. Intermediate formats covering a different number of detection sites 106, and asymmetric matrix layouts can also be fabricated. Some design considerations that went into the formats of FIG. 8 are outlined below.

| | FORMAT | | | |
|---|---|---|---|---|
| | 1K | 4K | 10K | 100K |
| NUMBER OF SITES | 32 × 32 = 1024 | 64 × 64 = 4096 | 100 × 100 = 10,000 | 316 × 316 ≈ 100,000 |
| SUBSTRATE SIZE | 3 inch square | 4 inch square | 4 inch square | 7.25 inch square |
| SITE SIZE | 890 $\mu$m square | 890 $\mu$m square | 635 $\mu$m square | 635 $\mu$m square |
| SITE PITCH | 2260 $\mu$m | 1488 $\mu$m | 965 $\mu$m | 558 $\mu$m |
| MIN. SITE VOLUME | 120 nL | 120 nL | 50 nL | 10 nL |
| MIN. SITE DEPTH | 200 $\mu$m | 200 $\mu$m | 200 $\mu$m | 150 $\mu$m |

In the illustration, detection site volume and depth are selected to help accommodate the insertion of beads on which synthetic or other chemistries are conducted.

Focusing on the 1K format, the pitch is the 2260 $\mu$m distance illustrated in FIG. 7. The area defined by the pitch further defines the amount of surface area that a given detection site 106 resides within. Thus, the product of the pitch between detection sites 106 in a row and the pitch between detection sites 106 in a column determines the size of the surface area on which an individual detection site 106 sits. The percentage of this surface area taken up by the area of each of the cell apertures is the area of the cell openings divided by the above-described product, times 100%.

It is useful in understanding how the planar substrate 106 is used to refer to Zanzucchi et al., "Liquid Distribution System," U.S. patent application Ser. No. 08/556,036, filed Nov. 9, 1995, which application is incorporated herein in its entirety by reference. This patent application describes a liquid distribution system ("LDS") that can deliver fluid from a number of reservoirs to all of a set of reaction cells or detection sites that are connected to the LDS and from additional reservoirs to a substantial subset of these reaction cells or detection sites. The liquid distribution device is designed for use in applications requiring a high density of reaction cells detection sites. In a preferred embodiment, the device uses electrode-based pumps that have no moving parts to transport fluid from the reservoirs to the reaction cells. The reaction cells or detection sites are preferably Format 1K Format 1K is a 1024 cell array symmetrically formed into 32 rows and 32 columns and having a reaction cell volume of at least about 120 nanoliter per detection site 106. For this size and array configuration, in a typical case, a detection site pitch of 2260 $\mu$m can be accommodated. A detection site configuration that satisfies volumetric and surface area requirements for fluid delivery, synthesis, assay and detection is 890 $\mu$m×890 $\mu$m. Using typical micromachining techniques suitable for production (for example see the description below of such a technique using chemical etching), the detection sites 106 have a fluid capacity of a minimum of about 120 nanoliters.

Format 4K

Format 4K is a 4096 cell array symmetrically formed into 64 rows and 64 columns and having a reaction cell volume capacity of at least about 120 nanoliter per detection site 106. For this size and array configuration, in a typical case, a detection site pitch of 1488 $\mu$m can be accommodated. The detection site configuration of 890 $\mu$m square of the 1K format is maintained. Using typical micromachining techniques suitable for production, the detection sites 106 have a fluid capacity of a minimum of about 120 nanoliters.

Format 10K

Format 10K is a 10,000 cell array symmetrically formed into 100 rows and 100 columns. Micromachined features are reduced in size from the 4K cell format. For use with this 10K plate, the associated liquid distribution system, for instance a liquid distribution system according to Zanzucchi et al.,"Liquid Distribution System," U.S. patent application Ser. No. 08/556,036, filed Nov. 9, 1995, is also fabricated with a correspondingly dense layout of fluid delivery capillaries. With such a dense layout of fluid delivery capillaries, a detection site pitch of 965 μm in the planar substrate 106 can be accommodated. The detection site configuration is adjusted for the more demanding requirements created by the higher density of detection sites. A 635 μm×635 μm detection site aperture is used. Using micromachining techniques suitable for production, the detection sites 106 have a fluid capacity of a minimum of about 50 nanoliters.

In certain preferred embodiments, the pitch of the individually addressable light sources is the same as that of the detection site pitch of one of the preferred planar substrate formates, or the pitch of the light sources is a whole-number multiple of detection site pitch such as a 2-fold, 3-fold, 4-fold, etc. multiple.

The detection site aperture is preferably substantially square or rectangular in profile to best accommodate an array format. The aperture can have rounded corners to accommodate the micromachining or molding/replication techniques used. Thus, "substantially" in this context means no more than the amount of rounding or irregularity in shape that can be expected when such structures are formed in glass by chemical etching, as predominately practiced commercially in 1995. Preferably, the circular features formed at the edges of the "rectangular" or "square" cells have radii no greater than the depth of the cell and the edges of the aperture of the cell are longer than the cell depth.

Figure 9:
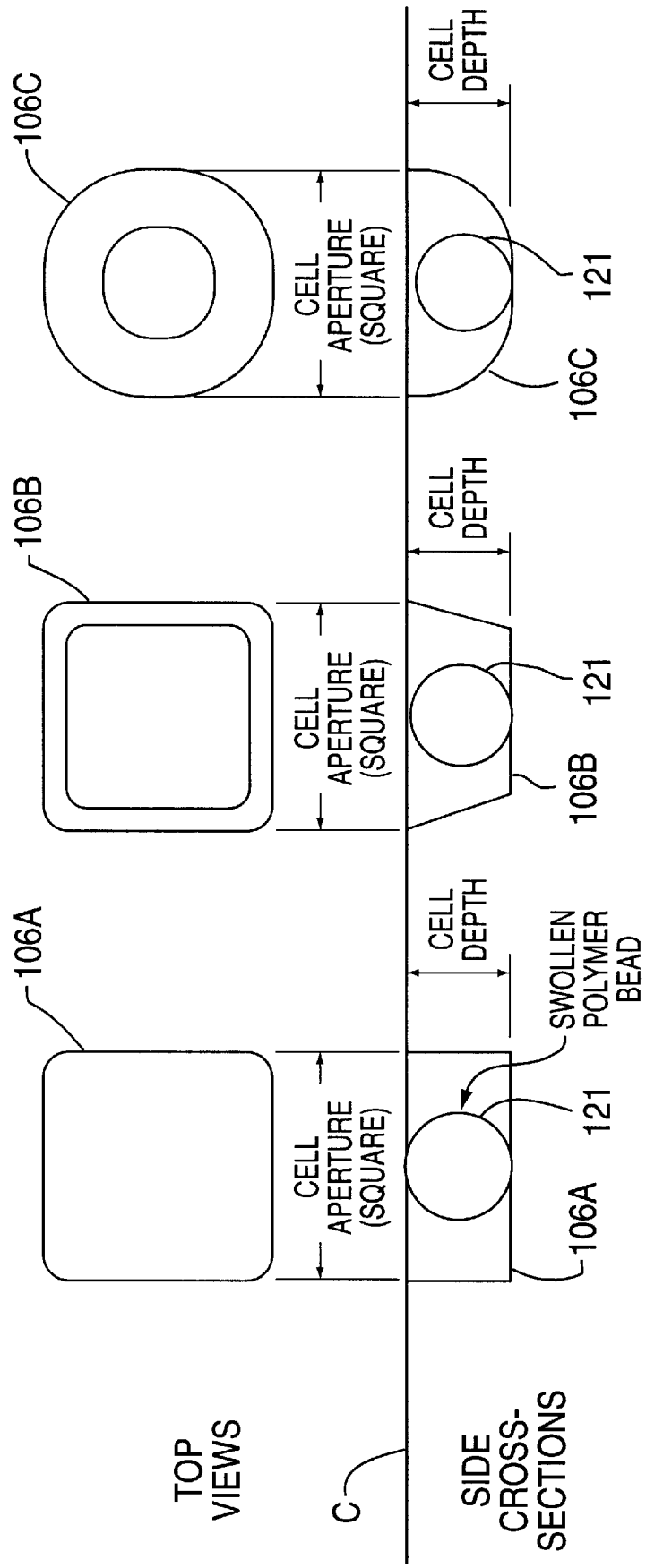
FIG. 9 shows three detection site geometries.

In FIG. 9, above line C are shown three top views for three different detection site 106 designs (first detection site 106A, second detection site 106B and third detection site 106C). Below line C are shown the side profiles of first detection site 106A, second detection site 106B and third detection site 106C. The profile of first detection site 106A illustrates the relatively sharp edge lines obtained by chemically etching a silicon substrate. The profile of second detection site 106B illustrates the relatively sharp edge lines obtained by laser etching a glass substrate. When chemically etching a glass substrate, the lines obtained are typically less sharp, as illustrated for detection site 106C. The detection site 106 cross-sectional profile can be of various shapes depending on the micromachining or replication technique but should preferably meet a minimum fluid volume capacity and must provide enough depth to accommodate experiments that require a bead 121 for use in syntheses or assays that require a solid support. Although a number of beads 121 per cell may be used, and although beads 121 of different sizes may be used depending on the experiment, the preferred design is based on providing adequate space for synthesis or other reaction on a single bead 121 of a defined maximum specified swollen diameter. In one use of the nanoliter plates, cell depths sufficient to accommodate swollen beads 121 of 200 μm diameter are used in formats 1K, 4K, 10K; and depths sufficient to accommodate swollen beads of 100 μm diameter are used in format 100K.

The detection site profile is achieved with micromachining, replicating, molding, or like fabrication methods, cells in a single substrate, or is achieved by combining multiple layers of substrates. The combining of layers can be achieved by known methods or, with appropriate substrates, with the field-assist sealing method described in Zhonghui H. Fan et al., U.S. Provisional Application Ser. No. P-89,876, titled "Field Assisted Glass-Glass Sealing," filed Nov. 7, 1995, which is incorporated herein in its entirety by reference. When the planar substrate is used for detection, optical requirements are important variables in the selection of cell construction, cross-sectional profile, and material. The planar substrate allows for the space between detection sites to be used to provide for fluid conduits and drains, electrical vias, sealing features, and the like. The planar substrate can be constructed of any material, material combinations, substrate thicknesses, and fabrication techniques, that suit the application.

Provision is preferably made on the planar substrate 105 to facilitate alignment (a) with the apparatuses that fabricate the planar substrate 105, and during assembly (b) with liquid distribution systems and other processing or detection equipment. For many cases mechanical alignment using three-pin registry is acceptable, and the edge alignment locations specified in FIG. 10 can be used. Although other alternatives can be used, the preferred method is to grind first edge notch 119A, second edge notch 119B and third edge notch 119C, for instance at the locations shown in FIG. 10. The use of such notches obviates the need to accurately machine all the edges of the planar substrate 105 and provides for a method of mechanically identifying the top and bottom of the planar substrate 105. The location of the center of the detection site patterns is defined in FIG. 10 by the intersection of lines D and E. The use of comparable notches in the manufacture of a liquid distribution system with which the planar substrate 105 allows equipment and tool manufacturers to coordinate their designs.

Figure 10:
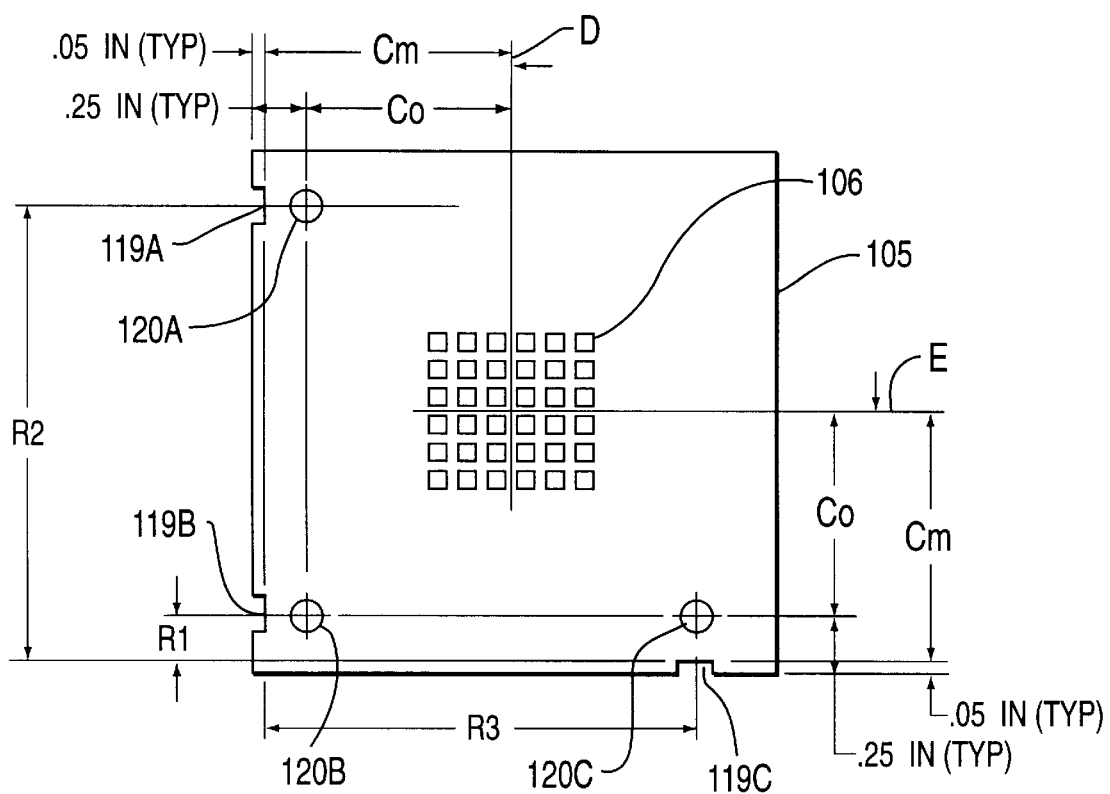
FIG. 10 shows the arrangement of alignment tools on a planar substrate.

In the illustrated planar substrate 105 of FIG. 10, examples of the distances represented by R1, R2, R3, Cm and Co are:

| FORMAT | R1 | R2 | R3 | Cm | Co |
|---|---|---|---|---|---|
| 1K | 0.25 in | 2.70 in | 2.70 in | 1.45 in | 1.25 in |
| 4K | 0.25 in | 3.70 in | 3.70 in | 1.95 in | 1.75 in |
| 10K | 0.25 in | 6.95 in | 6.95 in | 3.57 in | 3.37 in |

In some cases, optical alignment is preferable. The preferred location for the optical fiducials, such as first fiducial 120A, second fiducial 120B and third fiducial 120C, are illustrated in FIG. 10.

For all of the above-described embodiments, the preferred support material will be one that has shown itself susceptible to microfabrication methods, such as a microfabrication method that can form channels having cross-sectional dimensions between about 50 microns and about 250 microns. Such support materials include glass, fused silica, quartz, silicon wafer or suitable plastics. Glass, quartz, silicon and plastic support materials are preferably surface treated with a suitable treatment reagent such as a siliconizing agent, which minimizes the reactive sites on the material, including reactive sites that bind to biological molecules such as proteins or nucleic acids. In embodiments that require relatively densely packed electrical devices, a non-conducting support material, such as a suitable glass, is preferred. Preferred glasses include borosilicate glasses, low-alkali lime-silica glasses, vitreous silica (quartz) or other glasses of like durability when subjected to a variety of chemicals. Borosilicate glasses, such as Corning 0211, 1733, 1737 or 7740 glasses, available from Corning Glass Co., Corning, N.Y., are among the preferred glasses. For applications using fluorescence detection, materials having a low fluorescent background at the relevant excitation and emissions wavelengths are preferred.

The detection sites and horizontal channels and other structures of the planar substrates can be made by the following procedure. A plate is coated sequentially on both sides with, first, a thin chromium layer of about 500 Å thickness and, second, a gold film about 2000 angstroms thick in known manner, as by evaporation or sputtering, to protect the plate from subsequent etchants. A two micron layer of a photoresist, such as Dynakem EPA of Hoechst-Celanese Corp., Bridgewater, N.J., is spun on and the photoresist is exposed, either using a mask or using square or rectangular images, suitably using the MRS 4500 panel stepper available from MRS Technology, Inc., Acton, Mass. After development to form openings in the resist layer, and baking the resist to remove the solvent, the gold layer in the openings is etched away using a standard etch of 4 grams of potassium iodide and 1 gram of iodine ($I_2$) in 25 ml of water. The underlying chromium layer is then separately etched using an acid chromium etch, such as KTI Chrome Etch of KTI Chemicals, Inc., Sunnyvale, Calif.. The plate is then etched in an ultrasonic bath of $HF-HNO_3-H_2O$ in a ratio by volume of 14:20:66. The use of this etchant in an ultrasonic bath produces vertical sidewalls for the various structures. Etching is continued until the desired etch depth is obtained. Vertical channels are typically formed by laser ablation.

The gasket used to reversibly seal the planar substrate to a liquid distribution instrument that functions with the planar substrate can be affixed to the planar substrate, leaving openings for the detection sites and other structures, as needed. One method of attaching the gasket is screen-printing. The printed gasket can be made of silicone or another chemically-resistant, resilient material.

Alternatively, a multi-step compression-molding process that utilizes photolithography can be applied to affix the gasket. First, the top surface of the planar substrate, on which generally detection sites and other structures have been formed, is coated with a photoresist. Preferably, the photoresist layer is about 1 mil in thickness. The photoresist layer is treated by standard photolithography techniques to remove photoresist from those areas (the "gasket areas") away from the apertures of the cells where gasket material is desired. A layer of a flowable gasket material that can be cured to a resilient, elastomeric solid is applied. A platen having a polished surface, for instance a polished glass surface, is placed above the gasket material and pressure is applied to push the gasket material into the gasket areas and substantially clear the gasket material from the photoresist-coated areas. The gasket material is now cured. The photoresist is then dissolved, leaving the plate with a patterned gasket. The gasket material is "substantially" cleared if it is sufficiently cleared to allow the underlying photoresist to be dissolved.

In this process, the gasket material is any elastomeric material that is suitable for use in the above-described compression molding technique, that is, when cured, compatible with the chemistries that are to be practiced in the plate on which the gasket is formed, and that is, when cured, resistant to the solvents used to remove the photoresist. The gasket material is preferably silicone, such as RTV type silicone rubber (e.g., Silastic J, RTV Silicone Rubber available from Dow Corning, Midland, Mich.). The photoresist can be a film-type photoresist such that typically the structures on the plate will not be filled during the compression-molding process or a liquid-type photoresist such that the structures will temporarily be filled during the compression-molding process and etched away at the completion of the process. In some instances, it is desirable to treat the planar substrate, prior to the application of the photo-resist, with a primer for promoting the adhesion of the gasket material, such as 1200 RTV Prime Coat from Dow Corning, Midland, Mich. The planar substrate can also be roughened to promote the adhesion of the gasket material to the plate. For example, 5 micron roughness can be produced by lapping. The platen is preferably treated with a release-promoter, or a release promoter is incorporated into the gasket material, as it is in Silastic J silicone rubber. The compression-molding process can leave thin residues of gasket material at unwanted locations. These residues are laser cut away from the plate or, in some cases, are removed using a timed exposure to a solvent that dissolves the thin film of exposed gasket material residue without having substantial effect on the thicker layer of gasket material found at desired locations. This gasket can also be used as the optical blocking material of areas 107.

For planar substrates having about 1,000 to about 4,000 detection sites with a density of from about 10 detection sites per $cm^2$ to about 40 detection sites per $cm^2$, the corresponding array detector will preferably have pixels of about 10×10 $\mu m$ to about 100×100 $\mu m$ dimensions, and 1 to about 25 pixels per detection site. For example, a 256×256 pixels array detector will have in excess of 25 pixels per each of 1000 detection sites, namely 65 pixels per detection site.

For planar substrates having about 4,000 to about 10,000 detection sites with a density of from about 40 detection sites per $cm^2$ to about 100 detection sites per $cm^2$, the corresponding array detector will preferably have pixels of about 10×10 $\mu m$ to about 100×100 $\mu m$ dimensions, and 1 to about 25 pixels per detection site. For example, a 512×512 pixels array detector will have in excess of 25 pixels per each of 4000 detection sites, namely 65 pixels per detection site.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An apparatus for measuring the amount of light emitted or reflected from or transmitted through a first set of two or more detection sites on a planar substrate while spatially resolving the measurements from each first set detection site, the apparatus comprising:

a source of a light beam directed towards the planar substrate at a first angle;

one or more lenses for focusing light emitted or reflected from or transmitted through each of the first set detection sites and having a second angle having an angle offset from the first angle, onto a unique area of an array detector; and the array detector comprising a plurality of light responsive pixels, wherein for each of the first set detection sites there is at least one light responsive pixel that receives light emitted or reflected from or transmitted through that detection site and substantially no cross-talk from another detection site, and wherein substantially none of the light from the light source intersects with the array detector.

2. The apparatus of claim 1, wherein the detector array has sufficient light responsive pixels and is designed to work with a planar substrate having sufficient separation between the detection sites so that (a) there are first light responsive pixels of the detector array that are aligned to receive light emitted or reflected from or transmitted through the first set detection sites and (b) there are second light responsive pixels of the detector array that receive substantially no light because they are aligned with an area of blocking material, such that for each first set detection site there is a grouping of one or more first light responsive pixels receiving light therefrom and this grouping is separated from the grouping for any other first set detection site by at least one second light responsive pixel.

3. The apparatus of claim 2, wherein the detector array has sufficient light responsive pixels aligned with each first set detection site so that the light emitted or reflected from or transmitted through the detection site can be spatially resolved to detect differences across the detection sites in the quantity of light emitted or reflected therefrom.

4. The apparatus of claim 1, wherein the array detector comprises a photon-based imaging device.

5. The apparatus of claim 4, comprising the array detector which is selected from the group consisting of a charge coupled device (CCD), an intensified CCD array, a focal plane array, a photodiode array or photodetector array.

6. The apparatus of claim 1, wherein the apparatus is designed for use with planar substrates having detection sites that are concave depressions for holding liquid, wherein the surfaces on the depressions have a coating of one or more layers of material, wherein the coating is designed to reflect the light emitted or reflected from or transmitted through the detection sites.

7. The apparatus of claim 6, wherein the light source is designed to position beneath the planar substrate and the coating is designed to transmit the source light.

8. The apparatus of claim 1, wherein the apparatus is designed to detect light emitted or reflected from or transmitted through at least about 100 detection sites of the first set and has at least one light responsive pixel aligned with each detection site of the first set.

9. The apparatus of claim 1, wherein the source of light comprises at least one light producing device per detection site.

10. The apparatus of claim 1, wherein the one or more focusing lenses comprise a separate lenslet overlaid on the light responsive pixels aligned with each first set detection site.

11. The apparatus of claim 1, wherein the apparatus further comprises
an electronic storage device comprising a plurality of storage registers coupled to the array detector for storing the data from the array detector;
a processor having access to the stored data; and
a motor for moving the substrate, light source or array detector under the control of the processor,
wherein the processor is programmed to use one or more initial illuminations of the substrate with the source light to generate data which the processor uses to operate the motor to correct the alignment of the light source, first set detection sites and array detector.

12. The apparatus of claim 1, wherein the offset between the first and second angles is from at least about 10° to 180°.

13. An assay system comprising the apparatus of claim 1 and a plate having a first edge and a second edge and having at least about 1,000 uniformly sized reaction cells formed in its upper surface, wherein the density of the reaction cells is at least about 10 cells per $cm^2$, wherein the apparatus is designed to detect light emitted or reflected from or transmitted through the uniformly sized reaction cells.

14. An apparatus for measuring the amount of light emitted from a first set of two or more detection sites on a planar substrate while spatially resolving the measurements from each first set detection site, the apparatus comprising:
a source of a light beam having a first wavelength directed towards the planar substrate at a first angle;
one or more lenses for focusing light emitted from each of the first set detection sites and having a second angle onto a unique area of an array detector;
a filter interposed between the detection sites and the array detector, which filter selectively absorbs light of the first wavelength and transmits light emitted from the detection sites having a wavelength differing from the first wavelength; and
the array detector comprising a plurality of light responsive pixels, wherein for each first detection site there is at least one light responsive pixel that receives light emitted from that detection site and substantially no cross-talk from another detection site, wherein substantially none of the light from the light source intersects with the array detector.

15. The apparatus of claim 14, further comprising:
a first polarizing filter for polarizing the source light beam to a first polarity; and
a second polarizing filter for polarizing the light emitted from the detection sites to a second polarity, which is offset from the first polarity.

16. A method for measuring and spatially resolving the amount of light transmitted through a first set of two or more detection chambers or the amount of light emitted from the first set detection sites as a result of their illumination, wherein each chamber is separated by a blocking material that is opaque to the light and the density of first set detection sites is at least about 10 per $cm^2$, the method comprising
(1) providing an apparatus comprising:
a source of light directed towards the planar substrate at a transmission angle;
one or more lenses for focusing light from each first set detection chamber onto a unique area of an array detector; and
the array detector comprising a plurality of light responsive pixels, wherein for each first set detection chamber there is at least one light responsive pixel that receives light transmitted through that detection chamber and substantially no cross-talk from another detection chamber, and
(2) measuring light transmitted through the detection sites using the apparatus.

17. The method of claim 16, comprising operating the source of light to direct a pulse of light towards the first set detection sites and beginning to collect a light response in the array detector after the end of the light pulse while the source of light is not producing light.

18. The method of claim 16, wherein the apparatus is designed for use with planar substrates having detection sites that are concave depressions for holding liquid, wherein the surfaces on the depressions have a coating of one or more layers of material, wherein the coating is designed either to reflect the light emitted or transmitted from the detection sites or transmitted from the source of light.

19. An apparatus for measuring and spatially resolving the amount of light emitted from a first set of two or more detection sites arranged on a planar substrate with a density of at least about 10 detection sites per $cm^2$, the apparatus comprising:

one or more lenses for focusing light emitted from the first set detection sites, which light has a detection angle, onto an array detector; and the array detector comprising a plurality of light responsive pixels, wherein for each detection site there is at least one light responsive pixel that receives light emitted from that detection site and substantially no cross-talk from another detection site.

20. The apparatus of claim 19, further comprising the planar substrate, wherein either the planar substrate incorporates a scintillate adjacent to each detection site or the detection sites comprise chambers suitable for holding a fluid containing a scintillate.

* * * * *